United States Patent [19]

Watanabe et al.

[11] Patent Number: 5,532,199

[45] Date of Patent: Jul. 2, 1996

[54] CARRIER-SUPPORTED CATALYST FOR THE SYNTHESIS OF UNSATURATED ALDEHYDES AND UNSATURATED CARBOXYLIC ACIDS AND PROCESS FOR PREPARING THE SAME

[75] Inventors: Seigo Watanabe, Otake; Motomu Oh-Kita, Tokyo, both of Japan

[73] Assignee: Mitsubishi Rayon Co., Ltd., Tokyo, Japan

[21] Appl. No.: 359,430

[22] Filed: Dec. 20, 1994

Related U.S. Application Data

[63] Continuation-in-part of Ser. No. 76,978, Jun. 16, 1993, abandoned.

[30] Foreign Application Priority Data

Jun. 19, 1992 [JP] Japan ..................... 4-161410

[51] Int. Cl.$^6$ ..................... B01J 23/31
[52] U.S. Cl. ............ 502/311; 502/205; 502/212; 502/215; 502/255; 502/306; 502/307; 502/308; 502/309; 502/439
[58] Field of Search ............ 502/205, 212, 502/215, 255, 306, 307, 308, 309, 311, 439

[56] References Cited

U.S. PATENT DOCUMENTS

| | | | |
|---|---|---|---|
| 4,564,607 | 1/1986 | Yoneda et al. | 502/209 |
| 5,153,162 | 10/1992 | Kurimoto et al. | 502/209 |

FOREIGN PATENT DOCUMENTS

| | | |
|---|---|---|
| 0523727 | 1/1993 | European Pat. Off. . |
| A-56-44045 | 4/1981 | Japan . |
| A-57-130949 | 8/1982 | Japan . |
| A-59-31727 | 2/1984 | Japan . |
| A-59-173140 | 10/1984 | Japan . |
| A-60-28824 | 2/1985 | Japan . |
| B-2-36296 | 8/1990 | Japan . |

OTHER PUBLICATIONS

Laid Open Application No. JP-A-59-183832; ABSTRACT (10/1984).

*Primary Examiner*—Shrive Beck
*Assistant Examiner*—Timothy H. Meeks
*Attorney, Agent, or Firm*—Armstrong, Westerman, Hattori, McLeland & Naughton

[57] ABSTRACT

A carrier-supported catalyst for the synthesis of unsaturated aldehydes and unsaturated carboxylic acids, comprising a catalyst active substance comprising at least molybdenum and bismuth as its components, glass fiber having an average diameter in a range of more than 5 μm and not more than 200 μm and an average length in a range of from 50 μm to 1 mm, which is used as a carrier assistant in an amount of 0.5–50% by weight based on the catalyst active substance, and a carrier. The carrier-supported catalyst of this invention suffers no release or fall-off of the catalyst active substance from the carrier even if the catalyst supporting rate is increased. It also has high mechanical strength and is helpful for providing the objective product in a high yield. Further, the carrier-supported catalyst preparation process of this invention is capable of producing a carrier-supported catalyst having excellent mechanical strength and enabling high-yield production of an objective product, with ease and good reproducibility.

26 Claims, No Drawings

CARRIER-SUPPORTED CATALYST FOR THE SYNTHESIS OF UNSATURATED ALDEHYDES AND UNSATURATED CARBOXYLIC ACIDS AND PROCESS FOR PREPARING THE SAME

CROSS-REFERENCE

This is a continuation-in-part of application Ser. No. 08/076,978, filed Jun. 16, 1993; abandoned.

BACKGROUND OF THE INVENTION

1. Field of the Invention

The present invention relates to a carrier-supported catalyst used for the synthesis of unsaturated aldehydes and unsaturated carboxylic acids, more specifically a carrier-supported catalyst used for synthesizing acrolein and acrylic acid, or methacrolein and methacrylic acid through gas phase catalytic oxidation of propylene, isobutylene or tertiary butanol with molecular oxygen, and also to a process for preparing the same.

2. Description of the Related Art

A variety of methods have been proposed for the preparation of the catalysts used for the synthesis of unsaturated aldehydes and unsaturated carboxylic acids. Taking up the case where isobutylene or tertiary butanol is used as starting material, many proposals have been made, as in JP-A-57-130949, JP-A-59-31727 and JP-A-60-28824, regarding the catalysts used for the generation of methacrolein and methacrylic acids through catalytic oxidation of isobutylene or tertiary butanol in a high-temperature gas phase. In these proposals, however, little or no mention is made of carrier-supported catalysts, let alone a carrier-supported catalyst using glass fiber as carrier assistant.

It is known to incorporate inorganic fiber as a molding assistant in a catalyst used for molding. JP-B-2-36296 discloses a heteropoly-acid-based catalyst using whisker as molding assistant. It is stated in this publication that the above catalyst is unsuited for use as a carrier-supported catalyst as it is unable to produce a sufficient catalytic activity in use as a carrier-supported catalyst, and that the whisker used as molding assistant is preferably the one having an average diameter of not greater than 5 μm. On the other hand, according to the process for preparing a carrier-supported catalyst for the synthesis of unsaturated aldehydes and unsaturated carboxylic acids using molybdenum and bismuth as essential active components disclosed in the present invention, it is possible to obtain, with good reproducibility, a carrier-supported catalyst having a satisfactory catalytic activity by using glass fiber having an average diameter in the range of more than 5 μm and not more than 200 μm as carrier assistant. It is evident that the above publication is essentially different from the present invention.

In the prepation of a catalyst suitable for the production of acrolein and acrylic acid, or methacrolein and methacrylic acid through gas phase catalytic oxidation of propylene, isobutylene or tertiary butanol with molecular oxygen by a fixed bed reactor, in view of the fact that this reaction is an exothermic reaction, it is desirable to shape the catalyst active substance while defining the thickness of the catalyst layer for avoiding the undesirable rise of temperature due to heat accumulation in the catalyst layer. Definition of the catalyst layer thickness is also conducive to suppression of the collateral reactions of the product. Thus, a carrier-supported catalyst having an active substance supported on a carrier with a defined catalyst layer thickness proves in many cases favorable in terms of selectivity of the desired product.

A typical conventional carrier-supported catalyst producing method comprises dispersing a catalyst active substance or a catalyst precursor in a solvent to form a homogeneous solution or slurry, immersing a carrier therein or blowing said solution or slurry to the carrier to have said substance deposited on the carrier, and subjecting it to a heat treatment. This method, however, often proves unable to produce a catalyst with a satisfactory activity because of the limitation on the amount of the active substance that can be supported on a carrier.

It is known that the amount of the active substance supportable on a carrier can be increased by adding a hydroxide such as silica sol or alumina sol or an inorganic salt such as barium sulfate as carrier assistant. However, incorporation of such an additive material in the catalyst active substance tends to block the pores playing an important role for the reaction, resulting in a reduced catalyst performance. It is also known to add as binder a material that can be removed by a heat treatment, for example an organic compound such as oxalic acid, starch, polyvinyl alcohol, etc., or an inorganic salt such as ammonium nitrate. This method, however, has the problem that the mechanical strength of the obtained carrier-supported catalyst may be markedly reduced after removal of the binder, making the produced catalyst fail to have a sufficient strength for use as an industrial catalyst.

JP-A-59-173140 discloses a carrier-supported catalyst preparation method featuring use of whisker having an average diameter of not greater than 1 μm as a carrier aid. This method, however, is still unsatisfactory in respect of mechanical strength of the produced catalyst, and there is a possibility of causing release or degradation of the catalyst during transport or charging into a reactor. Further, whisker is costly as compared with the inorganic fibers having a relatively large diameter, such as glass fiber or asbestos, and is therefore economically disadvantageous for use in preparation of an industrial catalyst. Also, the above publication states that in case of using fibers having a relatively large diameter, such as glass fiber, as carrier aid, the spray nozzle may be blocked when a slurry containing a catalyst active substance and inorganic fiber is blown to the carrier by using a spray. However, the present inventors found that when a shower having a sufficiently large nozzle bore and fibers with good dispersibility in a liquid material are selected, it is possible to perform the carrier applying operation without inviting any problem even when using fibers having a relatively large diameter.

JP-A-56-44045 discloses a method for obtaining a surface-coated type catalyst by dispersing a catalyst active substance or a catalyst precursor and inorganic or organic fibers in a solvent to form a slurry, immersing an inactive base material in the slurry, and drying or firing the same. Also, in an example of this publication, there is shown a method for obtaining a surface-coated denitrated catalyst by using a cordierite honeycomb as inactive base material while using glass fiber of 13 μm in diameter as inorganic fiber. In the surface-coated catalyst producing method according to the above publication, since the catalyst substance is deposited on an inactive base material by means of immersion, the catalyst substance coating rate per run of coating operation is very low. In the case of a denitrated catalyst such as described in the above publication, the produced catalyst can well stand practical use even with a relatively low catalyst substance coating rate. However, in the the case of a catalyst to be used for the synthesis of unsaturated aldehydes and unsaturated carboxylic acids, when the catalyst active substance coating rate is of the degree specified in the above publication, it is impossible to obtain a catalyst having a sufficiently high activity required in practical use. It is therefore evident that the above publication is essentially different from the present invention.

Generally, further improvements are required of the carrier-supported catalysts from the industrial standpoint, particularly in terms of practicality of the production process, activity of the obtained carrier-supported catalyst, selectivity of the desired product and mechanical strength of the catalyst.

SUMMARY OF THE INVENTION

The present invention provides a carrier-supported catalyst usable for the advantageous synthesis of acrolein and acrylic acid, or methacrolein and methacrylic acid from propylene, isobutylene or tertiary butanol, and a process for preparing such a catalyst.

Specifically, the present invention is designed to provide a carrier-supported catalyst for the synthesis of unsaturated aldehydes and unsaturated carboxylic acids, comprising a catalyst active substance comprising at least molybdenum and bismuth as its components, glass fiber having an average diameter in a range of more than 5 µm and not more than 200 µm and an average length in a range of from 50 µm to 1 mm, used as carrier assistant in an amount of 0.5 to 50% by weight based on the catalyst active substance, and a carrier.

It is also envisaged in this invention to provide a process for preparing a carrier-supported catalyst for the synthesis of unsaturated aldehydes and unsaturated carboxylic acids, which comprises dispersing in a liquid material a catalyst active substance or catalyst precursor comprising at least molybdenum and bismuth as its components and glass fiber having an average diameter in a range of more than 5 µm and not more than 200 µm and an average length in a range of from 50 µm to 1 mm, said glass fiber being used as a carrier assistant in an amount of 0.5 to 50% by weight based on said catalyst active substance or catalyst precursor, thereby forming a slurry, and applying and depositing the resulting slurry on a carrier while at the same time vaporizing said liquid material to effect catalyst supporting on the carrier.

Generally, an increase of the catalyst supporting rate leads to an enhanced catalyst activity and an elongated catalyst life, but there are certain limitations to such improvements because of powdering and/or fall-off of the catalyst substance from the carrier. However, the carrier-supported catalyst for the synthesis of unsaturated aldehydes and unsaturated carboxylic acids according to the present invention suffers no release or fall-off of the catalyst active substance from the carrier even if the catalyst supporting rate is increased. The catalyst of this invention is also excellent in mechanical strength and helpful for providing the desired product in a high yield. The catalyst preparation process of this invention is capable of producing, with ease and good reproducibility, a carrier-supported catalyst having excellent mechanical strength and enabling high-yield production of the desired product.

PREFERRED EMBODIMENTS OF THE INVENTION

The materials constituting the catalyst active substance used in the present invention are not limited, but there are usually used the oxides and the compounds which can be turned into the oxides by strong heating, such as chlorides, hydroxides, sulfates, nitrates, carbonates, ammonium salts, and mixtures thereof. Especially preferred as the catalyst active substance are the composite oxides represented by the following formula:

$$Mo_aBi_bFe_cA_dX_eY_fZ_gO_h$$

wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, selenium, germanium, cerium, niobium, aluminum, titanium, zirconium, tungsten and antimony; Z represents at least one element selected from the group consisting of potassium, sodium, rubidium, cesium and thallium; a, b, c, d, e, f, g and h represent the atomic ratios of the respective elements, and when $a=12$, $0.1 \leq b \leq 5$, $0.1 \leq c \leq 5$, $1 \leq d \leq 12$, $0 \leq e \leq 10$, $0 \leq f \leq 10$ and $0.01 \leq g \leq 3$, and h is the number of the oxygen atoms necessary for satisfying the valences of the respective components.

The carriers usable in the present invention are not limited to the specific types; it is possible to use the generally employed carriers such as silica, alumina, silica-alumina, magnesia and titania. The shape of the carrier used in the present invention is also not specified; it may be, for instance, spherical, columnar, cylindrical or plate-like.

In accordance with the present invention, it is possible to easily prepare a carrier-supported catalyst having excellent mechanical strength and enabling high-yield production of the target product by using glass fibers having an average diameter in the range of more than 5 µm and not more than 200 µm, preferably from 10 µm to 200 µm, more preferably from 10 µm to 100 µm, and an average length in the range of from 50 µm to 1 mm, preferably from 50 µm to 250 µm, more preferably from 50 µm to 200 µm, as carrier assistant. Incorporation of such glass fibers as carrier assistant contributes to strengthening the catalyst layer on the carrier and markedly improving the mechanical strength of the carrier-supported catalyst. This leads to a markedly diminished possibility of release and degradation of the catalyst substance during transport or charging into a reactor. Further, since the catalyst pore volume is enlarged by the addition of said glass fiber, diffusion resistance in the catalyst is reduced to accordingly enhance the catalyst activity and also the collateral reactions are suppressed, resulting in an improved selectivity of the desired product.

When using glass fiber having an average diameter of not more than 5 µm, the obtained carrier-supported catalyst proves unsatisfactory in mechanical strength for use as an industrial catalyst. Use of glass fiber exceeding 200 µm in average diameter is also undesirable as such glass fiber is poor in dispersibility in liquid materials, making it impossible to obtain a homogeneous catalyst or giving rise to a possibility of causing blockade of the shower nozzle. With respect to the length of glass fiber used as carrier assistant, it is to be noted that too short a fiber length reduces the effect of reinforcement while too great a fiber length is inconvenient for handling. Therefore, the length of glass fiber used for said purpose is in the range of 50 µm to 1 mm on the average.

The glass fiber used as carrier aid in the present invention is preferably subjected to a pretreatment that makes the fiber substantially dispersible in a liquid material. Specifically, said glass fiber is preferably the one which can be well dispersed in a liquid material without causing aggregation of the individual fibers and can also be substantially passed through a screen with the openings equal in size to the shower nozzle hole.

The amount of glass fiber used as carrier aid in the present invention is preferably in the range of 0.5 to 50% by weight based on the catalyst active substance. When the content of inorganic fiber is less than 0.5% by weight, the effect of strengthening the catalyst layer tends to be unsatisfactory. When said content exceeds 50% by weight, the amount of the catalyst active substance in the carrier-supported catalyst is excessively reduced.

According to the present invention, even when the amount of the catalyst composition supported on the carrier is increased to some extent, the mechanical strength of the catalyst and the selectivity of the target product remain at a high level, owing to the reinforcing effect of the glass fiber and the effect of the increase of pore volume. Considering the mechanical strength of the catalyst and the selectivity of the desired product, it is desirable that the amount of the catalyst active substance to be supported on the carrier is in the range of 40–400 parts by weight to 100 parts by weight of the carrier.

Regarding the way of supporting the catalyst active substance on the carrier in the present invention, it is desirable to employ a method in which a catalyst active substance or a catalyst precursor and glass fiber are dispersed in a liquid material to form a slurry and this slurry is deposited on the carrier while at the same time vaporizing the liquid material. The "liquid material" used here is not specified; it is possible to use any liquid material, such as water, alcohols, ketones, esters, etc., which can be easily vaporized by heating and is harmless to the catalyst. Water is preferred for the industrial reason. For depositing said slurry on the carrier, it is recommended to use a shower having a nozzle hole diameter of 1–10 mm since there is no fear of blocking the nozzle hole with the glass fibers and also the operation is easy. When the nozzle hole is greater than 10 mm in diameter, although blockade of the nozzle with fibers becomes less likely to occur, the slurry deposition on the carrier tends to become non-uniform, making it harder to obtain a homogeneous carrier-supported catalyst.

As means for depositing the slurry on the carrier while simultaneously vaporizing the liquid material, although not specified in this invention, it is advisable, because of its simplicity, to employ a method in which the slurry is sprayed or blown to the carrier in a flowing state in a rotating drum, and at the same time the drum is heated from its outside or hot air or infrared rays are applied directly to the carrier to thereby vaporize the liquid material. When using this method, it is desirable that the shape of the carrier is spherical rather than plate-like.

According to the carrier-supported catalyst preparation process using the conventional impregnation method for catalyst supporting, the amount of the catalyst composition supported per process is small, and the catalytic activity of the obtained carrier-supported catalyst per unit weight tends to prove unsatisfactory. For increasing the supported amount of the catalyst in the above impregnation method, the steps of impregnation, catalyst supporting and drying must be repeated, so that the catalyst preparation process becomes very complicated and unfavorable for industrial application.

In the present invention, the catalyst active substance can be prepared by a known method. Generally, in the preparation process for an active substance of a catalyst used for the synthesis of unsaturated aldehydes and unsaturated carboxylic acids, there is included, in many cases, a step for a heat treatment at about 400°–600° C. In the present invention, the catalyst active substance obtained in the manner described above may be supported on a carrier by the above-described method to produce a carrier-supported catalyst, or a catalyst precursor before heat treatment may be supported on a carried by the above method, and the resulting carrier-supported substance may be heat treated at 400°–600° C.

In producing acrolein and acrylic acids or methacrolein and methacrylic acids through gas phase catalytic oxidation of propylene, isobutylene or tertiary butanol with molecular oxygen by using a catalyst obtained according to this invention, the molar ratio of propylene, isobutylene or tertiary butanol to oxygen is preferably 1:0.5–3. The starting material propylene, isobutylene or tertiary butanol is preferably diluted with an inert gas before use. The molecular oxygen used for the oxidation may be pure oxygen gas, but use of air is recommended for the economical reason. The reaction pressure applied in the process of this invention may range from normal pressure to several atm. The reaction temperature is preferably in the range of 200°–450° C.

The present invention is explained in more detail in the following Examples; however, it should be recognized that the scope of the present invention is not restricted to these Examples.

In the Examples and Comparative Examples given below, all the "parts" are by weight unless otherwise noted, and the analyses were made by gas chromatography. The reaction rate of the starting material propylene, isobutylene or tertiary butanol and the selectivity of the produced unsaturated aldehydes and unsaturated carboxylic acids are defined as follows:

Reaction rate of starting material (%) =

$$\frac{\text{number of moles of reacted material}}{\text{number of moles of supplied material}} \times 100$$

Selectivity of unsaturated aldehyde (%) =

$$\frac{\text{number of moles of produced unsaturated aldehyde}}{\text{number of moles of reacted material}} \times 100$$

Selectivity of unsaturated carboxylic acid (%) =

$$\frac{\text{number of moles of produced unsaturated carboxylic acid}}{\text{number of moles of reacted material}} \times 100$$

The packing and powdering rate of the carrier-supported catalyst is defined as follows. One thousand grams of the carrier-supported catalyst is dropped and packed into a stainless steel cylindrical container, 3 cm in inner diameter and 6 m long, set vertical to the horizontal direction, and the carrier-supported catalyst recovered from the bottom of the container is passed through a 14-mesh screen, with X g of the catalyst assumed remaining unpassed.

Packing and powdering rate $$(\%) = \frac{1,000 - X}{1,000} \times 100$$

EXAMPLE 1

Five hundreds parts of ammonium paramolybdate, 30.8 parts of ammonium paratungstate, 32.2 parts of cesium nitrate and 51.6 parts of antimony trioxide were added to 1,000 parts of water and heated with stirring (the resulting solution being called solution A-1). Meanwhile, 250 parts of a 60% nitric acid aqueous solution was added to 850 parts of water, and after homogenizing the resulting solution, 91.6 parts of bismuth nitrate was added and dissolved therein. To this solution, 286.0 parts of ferric nitrate, 343.1 parts of nickel nitrate, 68.7 parts of cobalt nitrate, 60.5 parts of magnesium nitrate, 70.2 parts of zinc nitrate and 7.3 parts of boric acid were added successively and dissolved (the resulting solution being called solution B-1). The solution B-1 was added to the solution A-1 to form a slurry, and this slurry was heated with stirring to vaporize the best part of water.

The resultantly obtained cake was dried at 120° C. for 10 hours, then calcined at 500° C. for 5 hours and pulverized to a particle size of 24 meshes or less.

The thus obtained catalyst active substance had the composition of the following formula:

$$Mo_{12}W_{0.5}Bi_{0.8}Fe_3Ni_5CO_1Mg_1Zn_1B_{0.5}Sb_{1.5}Cs_{0.7}O_x$$

wherein Mo, W, Bi, Fe, Ni, Co, Mg, Zn, B, Sb, Cs and O represent molybdenum, tungsten, bismuth, iron, nickel, cobalt, magnesium, zinc, boron, antimony, cesium and oxygen, respectively; the number suffixed behind each element symbol indicates the atomic ratio of the particular element; and x indicates the number of the oxygen atoms necessary for satisfying the valency of each component.

Then 400 parts of the obtained catalyst active substance and 20 parts of glass fiber having an average diameter of 10 μm and an average length of 200 μm were mixed in 600 parts of water to form a homogeneous slurry (which is called slurry C-1). This slurry C-1 was put to a 6.5-mesh screen. Almost all of the slurry could pass through the screen.

The slurry C-1 was gradually sprinkled on 300 parts of 4 mm diameter spherical alumina carrier flowing in a rotating drum by using a shower having a nozzle hole diameter of 3 mm, and at the same time the drum was heated from the outside thereof by a gas burner to evaporate water.

After the whole amount of the slurry C-1 has been sprinkled, the resulting product was dried at 130° C. for 3 hours.

The thus obtained carrier-supported catalyst was packed in a stainless steel reaction tube, and a gaseous mixture composed of 5% of isobutylene, 12% of oxygen, 10% of water vapor and 73% of nitrogen was passed through the catalyst layer with a contact time of 3.6 seconds and reacted at 365° C. The reaction rate of isobutylene was 95.5%, and the selectivity of methacrolein and that of methacrylic acid were 88.8% and 4.1%, respectively. The packing and powdering rate was 0.1%.

EXAMPLE 2

The procedure of Example 1 was followed except that the reactant was changed to tertiary butanol. As a result, the reaction rate of tertiary butanol was 100%, and the selectivity of methacrolein and that of methacrylic acid were 86.7% and 3.6%, respectively.

EXAMPLE 3

A carrier-supported catalyst was obtained by following the same procedure as in Example 1 except that the amount of glass fiber used was changed to 4 parts. By using this carrier-supported catalyst, the same reaction as in Example 1 was carried out. As a result, the reaction rate of isobutylene was 95.5%, and the selectivity of methacrolein and that of methacrylic acid were 88.8% and 4.1%, respectively, which are the same as the reaction results in Example 1. The packing and powdering rate was 0.2%. In this Example, the mechanical strength of the catalyst was slightly lower than that of the catalyst obtained in Example 1, but this presented no problem for practical use of the catalyst.

COMPARATIVE EXAMPLE 1

It was tried to produce a carrier-supported catalyst by following the procedure of Example 1 without using glass fiber. In this case, however, the catalyst layer on the carrier separated in the course of supporting process, and there can not be obtained a carrier-supported catalyst such as obtained in Example 1.

COMPARATIVE EXAMPLE 2

A carrier-supported catalyst was obtained according to the procedure of Example 1 by reducing the amount of glass fiber blended to 1 part. As a result of the reaction conducted in the same way as in Example 1 by using the obtained carrier-supported catalyst, the reaction rate of isobutylene was 95.2%, and the selectivity of methacrolein and that of methacrylic acid were 88.3% and 3.8%, respectively. Thus, the reaction results were slightly worse than Example 1. The packing and powdering rate was 4.5%, indicating a sharp reduction of mechanical strength of the catalyst as compared with Example 1.

COMPARATIVE EXAMPLE 3

A slurry (slurry D-1) was obtained in the same way as in Example 1 by dispersing in water a catalyst active substance and glass fiber which was same in shape as that used in Example 1 but bad in dispersibility. When the obtained slurry D-1 was put to a 5.5-mesh screen, about 2 parts of glass fiber aggregates remained unpassed on the screen.

The slurry which has passed through the screen and the aggregates which remained on the screen were again mixed, and after well stirring, it was tried to produce a carrier-supported catalyst in the same way as Example 1. However, the shower nozzle was blocked by the glass fiber aggregates in the course of catalyst supporting operation, and there could not be obtained a desired carrier-supported catalyst.

EXAMPLE 4

A catalyst active substance of the following composition was obtained in accordance with Example 1:

$$Mo_{12}Bi_1Fe_{2.6}Ni_2Co_4Zn_{0.5}Mn_{0.1}P_{0.1}Ge_{0.1}Sb_{0.8}Cs_{0.3}K_{0.1}O_x$$

wherein Mo, Bi, Fe, Ni, Co, Zn, Mn, P, Ge, Sb, Cs, K and O represent molybdenum, bismuth, iron, nickel, cobalt, zinc, manganese, phosphorus, germanium, antimony, cesium, potassium and oxygen, respectively; the number suffixed behind each element symbol indicates the atomic ratio of the particular element; and x is the number of the oxygen atoms necessary for satisfying the valency of each component.

Four hundreds parts of the obtained catalyst active substance and 30 parts of glass fiber having an average diameter of 10 μm and an average length of 200 μm were mixed in 600 parts of water to form a homogeneous slurry (slurry C-2). The slurry C-2 was subjected to a 5.5-mesh screen. Substantially all of the slurry could pass through the screen.

Then the slurry C-2 was gradually sprinkled on 200 parts of 4 mm-diameter spherical alumina carrier flowing in a rotating drum by using a shower having a nozzle hole diameter of 4 mm, and at the same time the drum was heated from the outside thereof by a gas burner to evaporate water.

After the whole amount of slurry C-2 has been applied, the carrier-supported substance was dried at 130° C. for 3 hours.

The thus obtained carrier-supported catalyst was packed in a stainless steel reaction tube, and a gaseous mixture composed of 5% of isobutylene, 12% of oxygen, 10% of water vapor and 73% of nitrogen was passed through the catalyst layer with a contact time of 3.6 seconds and reacted at 360° C. As a result, the reaction rate of isobutylene was 96.8%, and the selectivity of methacrolein and that of methacrylic acid were 87.8% and 3.7%, respectively. The packing and powdering rate was 0.1%.

COMPARATIVE EXAMPLE 4

It was attempted to prepare a carrier-supported catalyst in the same way as in Example 4 by using a shower with a nozzle hole diameter of 0.2 mm. However, the shower nozzle was blocked by the glass fiber aggregates in the course of catalyst supporting work, and there could not be obtained a desired carrier-supported catalyst.

COMPARATIVE EXAMPLE 5

A carrier-supported catalyst was produced according to the procedure of Example 4 by using a shower with a nozzle hole diameter of 20 mm. There was observed noticeable unevenness in sprinkling of the slurry over the catalyst. Also, the obtained carrier-supported catalyst was overly heterogeneous.

The reaction of Example 4 was carried out by using the thus obtained carrier-supported catalyst. As a result, the reaction rate of isobutylene was 96.2%, and the selectivity of methacryolein and that of methacrylic acid were 86.2% and 3.6%, respectively. The packing and powdering rate was 1.2%.

COMPARATIVE EXAMPLE 6

It was tried to prepare a carrier-supported catalyst according to the process of Example 4 by using glass fiber having an average diameter of 10 μm and an average length of 3 mm as carrier assistant. However, the shower nozzle was blocked by the glass fiber aggregates during the catalyst supporting operation, and it was unable to obtain a desired carrier-supported catalyst.

COMPARATIVE EXAMPLE 7

A slurry C-2 was prepared according to Example 4.

Two hundreds parts of 4 mm-diameter spherical alumina carrier was immersed in the slurry C-2, and after dehydrated well, the produced carrier-supported substance was dried at 130° C. for 3 hours. The thus obtained carrier-supported catalyst was measured to be 244.3 parts by weight.

The reaction in Example 4 was carried out by using the thus obtained carrier-supported catalyst. The reaction rate of isobutylene was 40.5%, indicating that this catalyst was an impractical low-activity catalyst.

COMPARATIVE EXAMPLE 8

A carrier-supported catalyst was obtained by following the same procedure as in Example 4 except that the proportion of glass fiber was changed to 700 parts.

The reaction in Example 4 was carried out by using the thus obtained carrier-supported catalyst. As a result, the reaction rate of isobutylene was 90.2%, while the selectivity of methacrolein and that of methacrylic acid were 86.9% and 3.4%, respectively. This catalyst was lower in activity than the catalyst obtained in Example 4.

EXAMPLE 5

Five hundreds parts of ammonium paramolybdate, 18.5 parts of ammonium paratungstate and 1.4 parts of potassium nitrate were added to 1,000 parts of water and heated with stirring to prepare a solution A-2. Meanwhile, 41.9 parts of a 60% nitric acid aqueous solution was added to 250 parts of water, and after homogenizing the resulting solution, 114.5 parts of bismuth nitrate was added and dissolved therein. To this solution, 95.3 parts of ferric nitrate, 309.0 parts of cobalt nitrate, 7.0 parts of zinc nitrate and 5.4 parts of telluric acid were added successively and dissolved by further adding 700 parts of water, forming a solution B-2. The solution B-2 was added to the solution A-2 to form a slurry, and this slurry was heated with stirring to evaporate the best part of water.

The resulting cake was dried at 120° C. for 10 hours, then calcined at 300° C. for 2 hours and pulverized to a particle size of 24 meshes or less.

The thus obtained catalyst precursor was of the following composition:

$$Mo_{12}W_{0.3}Bi_1Fe_1Zn_{0.1}Co_{4.5}K_{0.06}Te_{0.1}O_x$$

wherein Mo, W, Bi, Fe, Zn, Co, K, Te and O represent molybdenum, tungsten, bismuth, iron, zinc, cobalt, potassium, tellurium and oxygen, respectively; the number suffixed behind each element symbol is the atomic ratio of the particular element; and X is the number of the oxygen atoms necessary for satisfying the valency of each component.

Four hundreds parts of the above catalyst precursor and 100 parts of glass fibers having an average diameter of 6 μm and an average length of 60 μm were mixed in 600 parts of water to form a homogeneous slurry C-3. This slurry C-3 was put to a 3.5-mesh screen. Substantially all of the slurry could pass through the screen.

Then the slurry C-3 was gradually sprinkled over 200 parts of 4 mm-diameter spherical silica-alumina carrier flowing in a rotating drum by using a shower with a nozzle hole diameter of 6 mm, while at the same time hot air of about 200° C. was blown to said carrier to evaporate water.

After the whole amount of the slurry C-3 has been sprinkled, the obtained carrier-supported substance was calcined at 500° C. for 6 hours.

The thus obtained carrier-supported catalyst was packed in a stainless steel reaction tube, and a gaseous mixture composed of 5% of propylene, 12% of oxygen, 10% of water vapor and 73% of nitrogen was passed through the catalyst layer with a contact time of 3.6 seconds and reacted at 310° C. As a result, the reaction rate of propylene was 98.8% while the selectivity of acrolein and that of acrylic acid were 89.0% and 6.9%, respectively. The packing and powdering rate was 0.1%.

EXAMPLE 6

A slurry (D-2) was prepared by dispersing a catalyst active substance and glass fiber in water by following the procedure of Example 5 except for use of glass fiber having an average diameter of 100 μm and an average length of 1 mm. Substantially all of this slurry D-2 could pass through a 3.5-mesh screen.

By using this slurry D-2, a carrier-supported catalyst was produced according to the process of Example 5.

The reaction of Example 5 conducted by using the above carrier-supported catalyst showed that the reaction rate of propylene was 98.8% and the selectivities of acrolein and acrylic acid were 89.0% and 6.9%, respectively, the same results as Example 4. As noted from the packing and powdering rate of 0.3%, this catalyst was slightly lower in mechanical strength than the catalyst of Example 5 but had an enough strength to stand practical use.

COMPARATIVE EXAMPLE 9

A slurry (slurry E-1) was prepared by following the same procedure as in Example 5 except that aluminum borate whisker having an average diameter of 0.8 μm and a length of 10–30 μm was used as carrier assistant instead of glass fiber. Substantially all of the slurry E-1 could pass through a 3.5-mesh screen.

By using this slurry E-1, there was obtained a carrier-supported catalyst according to the process of Example 5.

The reaction of Example 5 was carried out by using the above catalyst, finding that the reaction rate of propylene was 98.2% while the selectivities of acrolein and acrylic acid were 88.5% and 6.0%, respectively. The reaction results were slightly inferior to those of Example 5. The packing and powdering rate was 3.4%, indicating a far lower mechanical strength of this catalyst than the catalyst of Example 5.

COMPARATIVE EXAMPLE 10

A slurry (slurry E-2) was prepared by following the same procedure as in Example 5 except that magnesia whisker having an average diameter of 6 μm and a length of 200 μm was used as carrier assistant instead of glass fiber. Substantially all of the slurry E-2 could pass through a 3.5-mesh screen.

By using this slurry E-2, there was obtained a carrier-supported catalyst according to the process of Example 5.

The reaction of Example 5 was carried out by using the above catalyst, finding that the reaction rate of propylene was 98.1% while the selectivities of acrolein and acrylic acid were 88.4% and 6.0%, respectively. The packing and powdering rate was 2.9%, indicating a far lower mechanical strength of this catalyst than the catalyst of Example 5.

COMPARATIVE EXAMPLE 11

A slurry (slurry E-3) was prepared by following the same procedure as in Example 5 except that glass fiber having an average diameter of 1 μm and a length of 100 μm was used. Substantially all of the slurry E-3 could pass through a 3.5-mesh screen.

By using this slurry E-3, there was obtained a carrier-supported catalyst according to the process of Example 5.

The reaction of Example 5 was carried out by using the above catalyst, finding that the reaction rate of propylene was 98.1% while the selectivities of acrolein and acrylic acid were 88.4% and 6.0%, respectively. The packing and powdering rate was 2.1%, indicating a far lower mechanical strength of this catalyst than the catalyst of Example 5.

What is claimed is:

1. A carrier-supported catalyst for the synthesis of unsaturated aldehydes and unsaturated carboxylic acids, comprising a catalyst active substance comprising at least molybdenum and bismuth as its components, glass fiber having an average diameter in a range of more than 5 μm and not more than 200 μm and an average length in a range of from 50 μm to 1 mm, said glass fiber being used as a carrier assistant in an amount of 0.5 to 50% by weight based on the catalyst active substance, and a carrier.

2. A catalyst according to claim 1, wherein the average diameter of said glass fiber is in a range of from 10 μm to 200 μm.

3. A catalyst according to claim 1, wherein the average diameter of said glass fiber is in a range of from 10 μm to 100 μm.

4. A catalyst according to claim 1, wherein the average length of said glass fiber is in a range of from 50 μm to 250 μm.

5. A catalyst according to claim 1, wherein the average length of said glass fiber is in a range of from 50 μm to 200 μm.

6. A catalyst according to claim 1, wherein a proportion of the catalyst active substance in the carrier-supported catalyst in a range of 40–400 parts by weight to 100 parts by weight of the carrier is used.

7. A catalyst according to claim 1, wherein the catalyst active substance comprises a composite oxide represented by the following formula:

$$Mo_aBi_bFe_cA_dX_eY_fZ_gO_h$$

wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, selenium, germanium, cerium, niobium, aluminum, titanium, zirconium, tungsten and antimony; Z represents at least one element selected from the group consisting of potassium, sodium, rubidium, cesium and thallium; and a, b, c, d, e, f, g and h indicate the atomic ratios of the respective elements, wherein when a=12, $0.1 \leq b \leq 5$, $0.1 \leq c \leq 5$, $1 \leq d \leq 12$, $0 \leq e \leq 10$, $0 \leq f \leq 10$, and $0.01 \leq g \leq 3$, and h is the number of the oxygen atoms necessary for satisfying the valency of each component.

8. A catalyst according to claim 2, wherein the catalyst active substance comprises a composite oxide represented by the following formula:

$$Mo_aBi_bFe_cA_dX_eY_fZ_gO_h$$

wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, selenium, germanium, cerium, niobium, aluminum, titanium, zirconium, tungsten and antimony; Z represents at least one element selected from the group consisting of potassium, sodium, rubidium, cesium and thallium; and a, b, c, d, e, f, g and h indicate the atomic ratios of the respective elements, wherein when a=12, $0.1 \leq b \leq 5$, $0.1 \leq c \leq 5$, $1 \leq d \leq 12$, $0 \leq e \leq 10$, $0 \leq f \leq 10$, and $0.01 \leq g \leq 3$, and h is the number of the oxygen atoms necessary for satisfying the valency of each component.

9. A catalyst according to claim 3, wherein the catalyst active substance comprises a composite oxide represented by the following formula:

$$Mo_aBi_bFe_cA_dX_eY_fZ_gO_h$$

wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, selenium, germanium, cerium, niobium, aluminum, titanium, zirconium, tungsten and antimony; Z represents at least one element selected from the group consisting of potassium, sodium, rubidium, cesium and thallium; and a, b, c, d, e, f, g and h indicate the atomic ratios of the respective elements, wherein when a=12, $0.1 \leq b \leq 5$, $0.1 \leq c \leq 5$, $1 \leq d \leq 12$, $0 \leq e \leq 10$, $0 \leq f \leq 10$, and $0.01 \leq g \leq 3$, and h is the number of the oxygen atoms necessary for satisfying the valency of each component.

10. A catalyst according to claim 4, wherein the catalyst active substance comprises a composite oxide represented by the following formula:

$$Mo_aBi_bFe_cA_dX_eY_fZ_gO_h$$

wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, selenium, germanium, cerium, niobium, aluminum, titanium, zirconium, tungsten and antimony; Z represents at least one element selected from the group consisting of potassium, sodium, rubidium, cesium and thallium; and a, b, c, d, e, f, g and h indicate the atomic ratios of the respective elements, wherein when a=12, $0.1 \leq b \leq 5$, $0.1 \leq c \leq 5$, $1 \leq d \leq 12$, $0 \leq e \leq 10$, $0 \leq f \leq 10$, and $0.01 \leq g \leq 3$, and h is the number of the oxygen atoms necessary for satisfying the valency of each component.

11. A catalyst according to claim 5, wherein the catalyst active substance comprises a composite oxide represented by the following formula:

$$Mo_aBi_bFe_cA_dX_eY_fZ_gO_h$$

wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, selenium, germanium, cerium, niobium, aluminum, titanium, zirconium, tungsten and antimony; Z represents at least one element selected from the group consisting of potassium, sodium, rubidium, cesium and thallium; and a, b, c, d, e, f, g and h indicate the atomic ratios of the respective elements, wherein when a=12, $0.1 \leq b \leq 5$, $0.1 \leq c \leq 5$, $1 \leq d \leq 12$, $0 \leq e \leq 10$, $0 \leq f \leq 10$, and $0.01 \leq g \leq 3$, and h is the number of the oxygen atoms necessary for satisfying the valency of each component.

12. A catalyst according to claim 6, wherein the catalyst active substance comprises a composite oxide represented by the following formula:

$$Mo_aBi_bFe_cA_dX_eY_fZ_gO_h$$

wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, selenium, germanium, cerium, niobium, aluminum, titanium, zirconium, tungsten and antimony; Z represents at least one element selected from the group consisting of potassium, sodium, rubidium, cesium and thallium; and a, b, c, d, e, f, g and h indicate the atomic ratios of the respective elements, wherein when a=12, $0.1 \leq b \leq 5$, $0.1 \leq c \leq 5$, $1 \leq d \leq 12$, $0 \leq e \leq 10$, $0 \leq f \leq 10$, and $0.01 \leq g \leq 3$, and h is the number of the oxygen atoms necessary for satisfying the valency of each component.

13. A process for preparing a carrier-supported catalyst for the synthesis of unsaturated aldehydes and unsaturated carboxylic acids, which comprises dispersing in a liquid material a catalyst active substance or a catalyst precursor comprising at least molybdenum and bismuth as it components and glass fiber having an average diameter in a range of more than 5 μm and not more than 200 μm and an average length in a range of from 50 μm to 1 mm, said glass fiber being used as a carrier assistant in an amount of 0.5–50% by weight based on said catalyst active substance or catalyst precursor, to form a slurry, and depositing said slurry on a carrier while at the same time vaporizing said liquid material, thereby supporting the catalyst active substance and glass fiber on the carrier.

14. A process according to claim 13, wherein the average diameter of said glass fiber is in a range of from 10 μm to 200 μm.

15. A process according to claim 13, wherein the average diameter of said glass fiber is in a range of from 10 μm to 100 μm.

16. A process according to claim 13, wherein the average length of said glass fiber is in a range of from 50 μm to 250 μm.

17. A process according to claim 13, wherein the average length of said glass fiber is in a range of from 50 μm to 200 μm.

18. A process according to claim 13, wherein a shower having a nozzle hole diameter in a range of 1–10 mm is used when depositing said slurry on the carrier.

19. A process according to claim 18, wherein the glass fiber used as carrier assistant can be well dispersed in the liquid material without causing aggregation of the individual fibers, and the slurry can substantially pass through a screen with a mesh size equal to the nozzle hole diameter of the shower.

20. A process according to claim 13, wherein the catalyst active substance comprises a composite oxide represented by the following formula:

$$Mo_aBi_bFe_cA_dX_eY_fZ_gO_h$$

wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, selenium, germanium, cerium, niobium, aluminum, titanium, zirconium, tungsten and antimony; Z represents at least one element selected from the group consisting of potassium, sodium, rubidium, cesium and thallium; and a, b, c, d, e, f, g and h indicate the atomic ratios of the respective elements, wherein when a=12, $0.1 \leq b \leq 5$, $0.1 \leq c \leq 5$, $1 \leq d \leq 12$, $0 \leq e \leq 10$, $0 \leq f \leq 10$, and $0.01 \leq g \leq 3$, and h is the number of the oxygen atoms necessary for satisfying the valency of each component.

21. A process according to claim 14, wherein the catalyst active substance comprises a composite oxide represented by the following formula:

$Mo_aBi_bFe_cA_dX_eY_fZ_gO_h$ wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, selenium, germanium, cerium, niobium, aluminum, titanium, zirconium, tungsten and antimony; Z represents at least one element selected from the group consisting of potassium, sodium, rubidium, cesium and thallium; and a, b, c, d, e, f, g and h indicate the atomic ratios of the respective elements, wherein when a=12, $0.1 \leq b \leq 5$, $0.1 \leq c \leq 5$, $1 \leq d \leq 12$, $0 \leq e \leq 10$, $0 \leq f \leq 10$, and $0.01 \leq g \leq 3$, and h is the number of the oxygen atoms necessary for satisfying the valency of each component.

22. A process according to claim 15, wherein the catalyst active substance comprises a composite oxide represented by the following formula:

$Mo_aBi_bFe_cA_dX_eY_fZ_gO_h$ wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, selenium, germanium, cerium, niobium, aluminum, titanium, zirconium, tungsten and antimony; Z represents at least one element selected from the group consisting of potassium, sodium, rubidium, cesium and thallium; and a, b, c, d, e, f, g and h indicate the atomic ratios of the respective elements, wherein when a=12, $0.1 \leq b \leq 5$, $0.1 \leq c \leq 5$, $1 \leq d \leq 12$, $0 \leq e \leq 10$, $0 \leq f \leq 10$, and $0.01 \leq g \leq 3$, and h is the number of the oxygen atoms necessary for satisfying the valency of each component.

23. A process according to claim 16, wherein the catalyst active substance comprises a composite oxide represented by the following formula:

$Mo_aBi_bFe_cA_dX_eY_fZ_gO_h$ wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, selenium, germanium, cerium, niobium, aluminum, titanium, zirconium, tungsten and antimony; Z represents at least one element selected from the group consisting of potassium, sodium, rubidium, cesium and thallium; and a, b, c, d, e, f, g and h indicate the atomic ratios of the respective elements, wherein when a=12, $0.1 \leq b \leq 5$, $0.1 \leq c \leq 5$, $1 \leq d \leq 12$, $0 \leq e \leq 10$, $0 \leq f \leq 10$, and $0.01 \leq g \leq 3$, and h is the number of the oxygen atoms necessary for satisfying the valency of each component.

24. A process according to claim 17, wherein the catalyst active substance comprises a composite oxide represented by the following formula:

$Mo_aBi_bFe_cA_dX_eY_fZ_gO_h$ wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, selenium, germanium, cerium, niobium, aluminum, titanium, zirconium, tungsten and antimony; Z represents at least one element selected from the group consisting of potassium, sodium, rubidium, cesium and thallium; and a, b, c, d, e, f, g and h indicate the atomic ratios of the respective elements, wherein when a=12, $0.1 \leq b \leq 5$, $0.1 \leq c \leq 5$, $1 \leq d \leq 12$, $0 \leq e \leq 10$, $0 \leq f \leq 10$, and $0.01 \leq g \leq 3$, and h is the number of the oxygen atoms necessary for satisfying the valency of each component.

25. A process according to claim 18, wherein the catalyst active substance comprises a composite oxide represented by the following formula:

$Mo_aBi_bFe_cA_dX_eY_fZ_gO_h$ wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, selenium, germanium, cerium, niobium, aluminum, titanium, zirconium, tungsten and antimony; Z represents at least one element selected from the group consisting of potassium, sodium, rubidium, cesium and thallium; and a, b, c, d, e, f, g and h indicate the atomic ratios of the respective elements, wherein when a=12, $0.1 \leq b \leq 5$, $0.1 \leq c \leq 5$, $1 \leq d \leq 12$, $0 \leq e \leq 10$, $0 \leq f \leq 10$, and $0.01 \leq g \leq 3$, and h is the number of the oxygen atoms necessary for satisfying the valency of each component.

26. A process according to claim 19, wherein the catalyst active substance comprises a composite oxide represented by the following formula:

$Mo_aBi_bFe_cA_dX_eY_fZ_gO_h$ wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, selenium, germanium, cerium, niobium, aluminum, titanium, zirconium, tungsten and antimony; Z represents at least one element selected from the group consisting of potassium, sodium, rubidium, cesium and thallium; and a, b, c, d, e, f, g and h indicate the atomic ratios of the respective elements, wherein when a=12, $0.1 \leq b \leq 5$, $0.1 \leq c \leq 5$, $1 \leq d \leq 12$, $0 \leq e \leq 10$, $0 \leq f \leq 10$, and $0.01 \leq g \leq 3$, and h is the number of the oxygen atoms necessary for satisfying the valency of each component.

* * * * *